United States Patent [19] [11] 4,406,086
Hayward [45] Sep. 27, 1983

[54] WHEAT AND METHOD OF PRODUCING THE SAME

[75] Inventor: Charles F. Hayward, Hutchinson, Kans.

[73] Assignee: Pioneer Hi-Bred International, Inc., Des Moines, Iowa

[21] Appl. No.: 358,307

[22] Filed: Mar. 15, 1982

[51] Int. Cl.$^3$ .............................................. A01H 1/02
[52] U.S. Cl. .................................. 47/58; 47/DIG. 1
[58] Field of Search ............................. 47/58, DIG. 1

[56] References Cited

U.S. PATENT DOCUMENTS 4,143,486  3/1979  Maan ........................................ 47/58
4,254,580  3/1981  Ferguson ................................. 47/58
4,351,130  9/1982  Rutger et al. ............................ 47/58

Primary Examiner—Robert E. Bagwill
Attorney, Agent, or Firm—Zarley, McKee, Thomte, Voorhees & Sease

[57] ABSTRACT

The method of producing wheat seeds comprising the steps of crossing plants grown from a first cross of 'Thorne' and 'Clarkan'; and crossing the plants from the seeds of Thorne/Clarkan with plants from the seed of 'Etoile de Choisy'; crossing seeds from a semi-dwarf mutant of the Etoile de Choisy//Thorne/Clarkan cross with plants grown from the seeds of CI 13390; and crossing the offspring therefrom with plants grown from seeds of 'Coker 68-15'; and selfing plants grown from the seeds of this cross. Selfing of plants after each cross to permit a pure line selection is done. The product of this method further defines the invention.

2 Claims, No Drawings

WHEAT AND METHOD OF PRODUCING THE SAME

BACKGROUND OF THE INVENTION

This invention relates to wheat and the method of producing the same.

Many varieties of wheat have been developed to accommodate different growing conditions, wheat usages, and disease and insect resistance. Winter wheat grown in colder climates varies from spring wheat in more moderate climates; hard wheat and soft wheat have different nutritional characteristics, and some wheat varieties are better suited to resist certain insects and diseases than others.

Despite the advances which have been made in wheat breeding, the wheat industry is lacking a wheat which yields consistently high, and which at the same time has good to excellent qualities in the areas of milling and baking; disease and insect resistance; and good straw strength.

It is therefore an object of this invention to provide a soft red winter wheat which has a high yieldability, and which at the same time possesses good milling and baking qualities; good disease and insect resistance; and good straw strength.

These and other objects will be apparent to those skilled in the art.

SUMMARY OF THE INVENTION

The method of this invention entails the selective sequential crossing of certain predetermined known wheat varieties in conjunction with the making of pure line selections after the plants of each cross are selfed. The basic crosses of this invention are as follows:

(1) Thorne/Clarkan.
(2) Etoile de Choisy with Thorne/Clarkan.
(3) Etoile de Choisy//Thorne/Clarkan with CI 13390.
(4) Coker 68-15 with Thorne/Clarkan//Etoile de Choisy/3/CI 13390.

This creates the genealogy of:
Coker 68-15/4/Etoile de Choisy//Thorne/Clarkan/3/CI 13390.

Plants from the last cross are selfed to provide the pure line of wheat of this invention which is referred to herein as variety '2550', *Triticum aestivum* L., em Thell, which is a soft red winter wheat.

DETAILED DESCRIPTION OF THE INVENTION

The wheat varieties used in the method of this invention, resulting in the product of this invention, are known in the art and are identified herein by the designations by which they are identified in the art. Further details of the genealogy of these varieties are a matter of public record and are readily available.

The initial step of this invention is to cross the plants of Thorne and Clarkan. The plants from the seed of this cross were selfed to permit a pure line selection which reflected the characteristics of the cross as distinguished from the characteristics of either parent.

Plants from the pure line selection of the preceding cross were then crossed with plants from the French variety, Etoile de Choisy. The cross between Etoile de Choisy//Thorne/Clarkan has been made in the prior art and does not of itself constitute a part of this invention. Plants from this cross were selfed, and seed was selected from a semi-dwarf mutant. Plants from the seed of this mutant were then crossed with plants from the seed of CI 13390. Through selfing, a pure line selection from this cross was crossed to Coker 68-15.

Selections were made from the $F_2$ generation of the last-described cross for plant height, straw strength, maturity and head type. The $F_3$ generation was then made from these selections, and further selections were then made for winterhardiness, height, maturity, straw strength, disease resistance and for plant and head type. Seed from this selection was used for the $F_4$ generation which was examined particularly for yieldability. A reselection was made from an $F_5$ generation and traced to a single $F_4$ plant. Plants from this selection were tested in yield trials and for milling and baking quality. Final selection was made in the $F_8$ generation and this selection is variety 2550, *Triticum aestivum* L., em Thell.

2550 has shown uniformity and stability for all of the traits described in Table 1, with the only variant observed and expected is a very low frequency of awns ($<1/30,000$).

TABLE I

OBJECTIVE DESCRIPTION OF VARIETY

Kind: Common
Type: Winter, soft, red
Season - Number of days from emergence to:
   (a) First flowering: 229
   (b) Last flowering: 236
Maturity (50%) Flowering: 2 days later than 'Arthur'
Plant Height: 95 cm high (4 cm shorter than Arthur)
Plant Coloring at Booting: Blue green
Stem:
   (a) Anthocyanin: Absent
   (b) Hairiness of last internode of rachis: Absent
   (c) Number of nodes: 4
   (d) Waxy bloom: Present
   (e) Internodes: Hollow
   (f) Cm internode length between flag leaf and leaf below: 22
Auricles:
   (a) Anthocyanin: Absent
   (b) Hairiness: Absent
Leaf:
   (a) Flag leaf at booting stage: Recurved
   (b) Hairs of first leaf sheath: Absent
   (c) Width of first leaf below flag leaf: 12 mm
   (d) Flag leaf: Not twisted
   (e) Waxy bloom of flag leaf sheath: Present
   (f) Length of first leaf below flag leaf: 23 cm
Head:
   (a) Density: Lax
   (b) Awnedness: Awnleted
   (c) Color at maturity: Yellow
   (d) Length: 8 cm
   (e) Shape: Tapering
   (f) Width: 12 mm
Glumes at Maturity:
   (a) Length: Long (CA. 9 mm)
   (b) Shoulder shape: Oblique
   (c) Width: Wide (CA 4 mm)
   (d) Beak: Acute
Coleoptile Color: White
Juvenile Plant Growth Habit: Semi-erect
Seed:
   (a) Shape: Ovate
   (b) Brush: Medium
   (c) Phenol reaction: Very dark brown, nearly black, similar to 'Monon'
   (d) Color: Red
   (e) Length: 7 mm
   (f) Width: 3 mm
   (g) Cheek: Rounded
   (h) Brush: Not collared
   (i) Weight per 1000 seeds: 36 gm
Seed Crease:

TABLE I-continued

OBJECTIVE DESCRIPTION OF VARIETY (a) Width: 60% or less of kernel 'Winoka'
(b) Depth: 20% or less of kernel 'Scout'

Disease
   (a) Stem rust: Susceptible
   (b) Loose smut: Susceptible
   (c) Soil Borne Mosaic Virus: Resistant
   (d) Spindle Streak Mosaic Virus: Resistant Insect:
   (a) Aphid: Resistant
   (b) Hessian fly: Susceptible to races B, D, E and G; resistant to races GP, A, C and F Resemblance to Known Varieties:

| Character | Name of Variety |
| --- | --- |
| Plant tillering | 'Abe' |
| Leaf size | Abe |
| Leaf color | 'McNair 1003' |
| Leaf carriage | Abe |
| Seed size | 'Pioneer Variety S76' |
| Seed shape | Pioneer Variety S76 |
| Coleoptile elongation | Pioneer Variety S76 |
| Seedling pigmentation | Pioneer Variety S76 |

Deposit of 2550 seeds has been made prior to the filing of this application at the National Seed Storage Laboratory, Colorado State University, Fort Collins, Colo., under Laboratory Accession No. TV 24904 and NSSL Serial Number 163525.

As reflected in the above Table 1, the flowering date of 2550 is two days later than the variety Arthur and one day earlier than Pioneer variety S76. At Tipton, Ind., when seeded about October 1, average first flowering is May 27 or about 229 days after emergence. Last flowering averages about seven days later. Environmental factors influence flowering of varieties differently.

2550 has averaged 95 cm in height, which is about 4 cm shorter than Arthur and Pioneer variety S76.

The plant color of 2550 at booting stage is a distinct blue-green while Arthur is green and 'Beau' is dark green. Another color of 2550 is yellow, similar to Pioneer variety S76.

Anthocyanin has been absent in the stem of 2550. A heavy waxy bloom occurs on the stem. Internodes of 2550 are hollow. At maturity, the stems are yellow and strong. Normally four stem nodes are present above ground. Internode length between flag leaf and leaf below is about 22 cm. The last internode of the rachis is free of hairiness.

Auricles of 2550 are lacking in anthocyanin and are free of hairiness.

Flag leaves are generally recurved at booting and are not twisted. Hairs are absent from the first leaf sheath. A heavy waxy bloom occurs on the flag leaf sheath. The first leaf below the flag leaf averages about 12 mm wide and 23 cm long.

Spikes are generally mid-dense to lax, tapering, awnleted, yellow and generally nodding at maturity. The apical awnlets are rough and about 15–20 mm long. Spike width and length averages about 12 mm and 8 cm, respectively. However, spike width and length are variable with plant population and level of production.

The glumes of 2550 are long and wide, glabrous and generally the shoulders are oblique. The beaks are acute.

The coleoptile color is white and seedling anthocyanin is absent. Juvenile plant growth habit is semi-erect.

The kernels are red in color, ovate in shape, with rounded cheeks and a shallow crease. The brush is not collared and medium in size. The embryo is large in size. The kernels average 7 mm long and 3 mm wide and weight about 36 g per 1000. Phenol reaction is very dark brown, nearly black, similar to Monon.

2550 is moderately resistant to leaf rust (*Puccinia recondita* f. sp. *tritici*) and susceptible to stem rust (*P. graminis* f. sp. *tritici*) races currently common in the soft red winter wheat region. 2550 has not been tested for specific races of leaf rust nor has it been tested for stripe rust (*P. striiformis*), bunt (*Tilletia foetlda* and *T. caries*) and loose smut (*Ustilago tritici*). While susceptible to powdery mildew (*Erysiphe graminis* f. sp. *tritici*), the progression of the disease up the plant is slow.

2550 has a good level of resistance to soil borne mosaic virus, spindle streak mosiac virus and barley yellow dwarf virus. In testing for BYDV, 'Clintland 64' oat variety was used as a very susceptible check, Abe as the susceptible wheat variety check and 'Hart' as a wheat variety check with notable resistance. Results were as follows: Clintland 64-6; Abe-5; Hart-3; 2550-2.

2550 is resistant to Hessian fly races GP, A, C and F and susceptible to races B, D, E and G. 2550 has not been tested for sawfly, greenbug and cereal leaf beetle.

2550 is most similar to the soft red winter Pioneer variety S76 in a number of plant and seed characteristics. Certain similarities are expected since one half the parentage of 2550 and S76 is the same. However, there are a number of distinguishable differences between the two varieties. The most easily recognized difference is that S76 is awned and 2550 is awnleted. Plant height of 2550 averages about 4 cm shorter. Less notable differences between the two varieties are: The plant color of 2550 at booting stage is a distinct blue-green, while S76 is green to slight blue-green. A heavy waxy bloom occurs on the stem and flag leaf sheath of 2550 while only a light and moderate waxy bloom occurs on the stem and flag leaf sheath respectively of S76. Shoulders of the glume are oblique on 2550 and wanting on S76. Beaks are acute on 2550 and acuminate on S76.

As reflected in Table 2, 2550 is higher yielding and has a higher level of field resistance to prevalent races of leaf rust and powdery mildew than S76. S76 has better straw strength and more resistance to spindle streak mosaic virus and soil borne mosaic virus than 2550.

TABLE 2

Performance of Pioneer Varieties 2550 and 2553 and Standard Varieties Grown in Elite Yield Trials

| Variety | Yield bu/acre (72)*** | Test Weight lbs/bu (51) | Height cm (48) | Days to Flowering after 4/1 (39) | Lodging** Score (45) | Powdery** Mildew (13) | Leaf** Rust (9) | Spindle Streak** Mosaic Virus (3) | Soil Borne** Mosaic Virus (4) |
| --- | --- | --- | --- | --- | --- | --- | --- | --- | --- |
| 2550 | 71.4 | 57.6 | 95 | 55.4 | 6.5 | 6.1 | 8.0 | 7.0 | 6.2 |
| 2553 | 68.0 | 59.0 | 96 | 55.7 | 8.2 | 3.8 | 6.8 | 8.0 | 7.0 |
| S76 | 63.4 | 57.8 | 99 | 56.4 | 7.5 | 4.1 | 6.4 | 8.3 | 7.5 |
| S78 | 62.6 | 57.5 | 93 | 57.2 | 6.8 | 3.5 | 7.3 | 8.7 | 5.8 |
| Hart | 62.4 | 57.8 | 103 | 55.1 | 6.7 | 4.1 | 5.7 | 7.7 | 7.0 |
| Abe | 60.2 | 58.7 | 99 | 54.3 | 4.7 | 6.2 | 4.5 | 4.7 | 4.2 |

TABLE 2-continued

Performance of Pioneer Varieties 2550 and 2553 and Standard Varieties Grown in Elite Yield Trials

| Variety | Yield bu/acre (72)*** | Test Weight lbs/bu (51) | Height cm (48) | Days to Flowering after 4/1 (39) | Lodging** Score (45) | Powdery** Mildew (13) | Leaf** Rust (9) | Spindle Streak** Mosaic Virus (3) | Soil Borne** Mosaic Virus (4) |
|---|---|---|---|---|---|---|---|---|---|
| Beau | 59.9 | 59.4 | 99 | 54.8 | 6.2 | 6.6 | 4.9 | 5.0 | 4.0 |
| Sullivan | 58.1 | 59.2 | 103 | 53.6 | 4.5 | 6.2 | 5.5 | 4.0 | 5.8 |

**Scale 1-9 where 9 = excellent or resistant and 1 = poor or 100% susceptible
***Number in parenthesis - replications.

Since half the parentage of 2550 is Coker 68-15, there are similarities between 2550 and Coker 68-15. These varieties are readily distinguishable by their level of winterhardiness. In winterhardiness tests (1-9 scale with 9 being most winterhardy), the average readings were 7.0 and 3.0 for 2550 and Coker 68-15 respectively.

As shown in Table 2, 2550 has an excellent yield record when compared with the current leading soft red winter wheat varieties, including approximately a 10% increase in yield over Pioneer variety S76. In the presence of soil borne mosaic virus or spindle streak mosaic virus, 2550 has a pronounced yield advantage over susceptible varieties. Short plant height and good straw strength give 2550 excellent resistance to lodging, and this enhances yieldability.

The milling and baking qualities of 2550 are generally equivalent to current varieties commonly grown in the SRW region. Flour protein is consistently lower (desirable) than Abe. It has better protein levels and break flour yields than Pioneer variety S76, as shown in the following Table 3.

TABLE 3

Results of Quality Testing on 2550 (Pioneer Wheat Quality Lab)

| Test/Sample | Flour Yield (%) | Break Flour (%) | Flour Protein (%) | AWRC (%) | Cookie Diam. (cm.) | PSI (%) |
|---|---|---|---|---|---|---|
| Test I - Average Data (2 locations) | | | | | | |
| 2550 | 67.6 | 36.4 | 10.7 | 55.3 | 17.9 | 45.6 |
| Abe | 66.7 | 37.3 | 12.5 | 53.3 | 17.9 | 51.9 |
| Avg. all checks | 67.4 | 37.0 | 12.3 | 53.7 | 17.8 | 52.2 |
| Test II - Average Data (3 locations) | | | | | | |
| 2550 | 66.0 | 35.9 | 7.5 | 54.3 | 19.7 | 44.8 |
| Abe | 68.2 | 35.4 | 8.3 | 51.4 | 19.2 | 51.1 |
| Avg. all checks | 65.6 | 35.3 | 8.7 | 53.9 | 19.3 | 48.8 |
| Test III - Average Data (6 locations) | | | | | | |
| 2550 | 66.1 | 34.8 | 7.6 | 56.2 | 19.5 | 43.7 |
| Abe | 67.2 | 34.1 | 8.5 | 53.8 | 19.5 | 46.3 |
| Avg. all checks | 66.3 | 33.8 | 8.7 | 54.2 | 19.5 | 44.8 |
| Test IV - Average Data (7 locations) | | | | | | |
| 2550 | 70.0 | 38.1 | 9.4 | 55.4 | 18.8 | 32.7 |
| Abe | 70.2 | 36.1 | 10.4 | 53.7 | 18.7 | 32.2 |
| Avg. all checks | 69.1 | 36.2 | 10.4 | 54.4 | 18.6 | 31.7 |

NOTES:
Locations tested include: Loogootee, Illinois; Fort Branch and Tipton, Indiana; and Tiffin, Ohio.
Check samples include various combinations of: Abe, Beau, Coker 68-15, Double Crop, Funk W504, Hart, McNair 3001, Oasis, Roland, Ruler, Sullivan and Titan.
Methods:
Milling = Brabender Quadramat Sr. Mill
Protein - Udy method
AWRC - Micro method on milled flour
Cookie diameter - total diameter of two cookies
PSI - Through '79 - Sonic sifter
    - From '80 on - A B grinder, sieve shaker While making the crosses of the method of this invention, the variety used as the male or female is not deemed to be crucial, although the first designated variety is deemed to be the female parent, and the second variety is the male parent. The crosses are accomplished by conventional methods whereby male anthers are removed from a plant to create a female plant; the head of the female plant is then covered to protect contamination; and then pollen grain from anthers of the desired male plant are deposited on the stigmas of the female plant which remains covered to prevent contamination.

The principal advantage of 2550 is its high yieldability which demonstrates a substantial improvement over existing varieties. This high yieldabilty, coupled with good milling and baking qualities, good disease and insect resistance, and good straw strength, provides a superior wheat. Accordingly, this invention is seen to accomplish at least all of its stated objectives.

What is claimed is:

1. A method of producing wheat seeds, comprising:
   (a) crossing plants grown from seeds of Thorne and Clarkan;
   (b) developing a pure line from the seeds produced in step "a", and crossing plants from such line with plants grown from seeds of Etoile de Choisy;
   (c) developing a pure line from the seeds from a semi-dwarf mutant produced in step "b", and crossing plants from such line with plants grown from seeds of CI 13390;
   (d) developing a pure line from the seeds produced in step "c" and crossing plants from such line with plants grown from seeds of Coker 68-15;
   (e) and developing a pure line from the seeds produced in step "d" and harvesting the seed resulting from said line.

2. Seed produced in accordance with the method of claim 1.

* * * * *